United States Patent [19]

Kroenke

[11] 4,129,540

[45] Dec. 12, 1978

[54] SMOKE RETARDED POLYMER COMPOSITIONS CONTAINING AMINE MOLYBDATES

[75] Inventor: William J. Kroenke, Brecksville, Ohio

[73] Assignee: The B. F. Goodrich Company, Akron, Ohio

[21] Appl. No.: 841,182

[22] Filed: Oct. 11, 1977

Related U.S. Application Data

[63] Continuation-in-part of Ser. No. 770,168, Feb. 14, 1977, Pat. No. 4,053,455.

[51] Int. Cl.$^2$ .......................... C08K 5/34; C08K 5/17

[52] U.S. Cl. .................. 260/28.5 A; 260/28.5 AV; 260/28.5 B; 260/28.5 D; 260/45.75 R; 260/45.7 R; 260/42.34; 260/42.44; 260/42.41; 260/42.45; 260/42.46; 260/42.47

[58] Field of Search ................. 260/28.5 A, 28.5 AV, 260/28.5 B, 28.5 D, 45.75 R, 42.34, 42.39, 42.44, 42.41, 42.45, 42.46, 42.47, 45.7 RL

[56] References Cited

U.S. PATENT DOCUMENTS

| | | | |
|---|---|---|---|
| 3,821,151 | 6/1974 | Mitchell | 260/45.75 R |
| 3,845,001 | 10/1974 | Mitchell | 260/45.75 R |
| 4,053,453 | 10/1977 | McRowe et al. | 260/45.75 R |

*Primary Examiner*—V. P. Hoke
*Attorney, Agent, or Firm*—Charles A. Crehore

[57] ABSTRACT

Amine molybdates retard smoke formation effectively during burning of certain organic polymers.

19 Claims, No Drawings

SMOKE RETARDED POLYMER COMPOSITIONS CONTAINING AMINE MOLYBDATES

CROSS REFERENCE TO RELATED APPLICATION

This is a continuation-in-part of my copending U.S. patent application Ser. No. 770,168 filed Feb. 14, 1977 now U.S. Pat. No. 4,053,455.

BACKGROUND OF THE INVENTION

The fact that an additive is a flame retardant does not necessarily mean that it will have good smoke retardant properties, as is well known to those skilled in the art. U.S. Pat. Nos. 3,821,151, 3,845,001 and 3,870,679 teach use of certain molybdenum compounds, alone or on combination with other compounds, as smoke retardants in PVC. The specific compounds listed therein suffer from the disadvantages that most, such as $MoO_3$, are colored compounds giving an unsatisfactory tint to compositions in which they are used. Even white or lightly colored molybdenum compounds such as the ammonium or sodium molybdates tend to discolor the PVC compounds, and also give less satisfactory smoke reduction than $MoO_3$.

New, highly effective smoke retarded polymer compositions are desired.

SUMMARY OF THE INVENTION

Amine molybdates are effective smoke retardant additives for polymers selected from the group consisting of polyamides, polychloroprene, polymonoolefins, halogenated and chlorosulfonated polymonoolefins, polyphenylene oxides, polysulfones, poly(vinyl acetate), epihalohydrin polymers, and polymers of acrylonitrile alone or with butadiene and/or styrene. Melamine molybdate is preferred, since it is both white and highly effective as a smoke retardant. Melamine molybdate also processes easily without discoloring the polymers.

DETAILED DESCRIPTION

Amine Molybdates.

The additive amine molybdates used in this invention may be polycrystalline or amorphous fine powders, preferably with an average particle size from about 0.01 to about 800 microns, more preferably from about 0.1 to about 200 microns, and even more preferably from about 0.5 to about 50 microns. The amine molybdates are used in smoke retardant amounts, typically from about 0.01 to about 20 parts by weight, more preferably from about 1 to about 10 parts by weight, per 100 parts by weight of polymer. Supporting media such as $SiO_2$, $Al_2O_3$ and the like may be used for the smoke retardant additives and in many cases are preferred, since additive surface area is increased greatly for smoke reduction purposes.

Amine molybdates may be produced by reacting a suitable amine with a molybdenum compound such as $MoO_3$, molybdic acid or a molybdenum salt. Molybdenum salts include ammonium molybdate, ammonium dimolybdate, ammonium heptamolybdate (also called ammonium paramolybdate), ammonium octamolybdate, sodium molybdate or the like. Ammonium molybdates are preferred and include ammonium molybdate $[(NH_4)_2MoO_4]$ itself, ammonium dimolybdate $[(NH_4)_2Mo_2O_7]$, ammonium heptamolybdate $[(NH_4)_6Mo_7O_{24}.4H_2O]$, and ammonium octamolybdate $[(NH_4)_4Mo_8O_{26}.5H_2O]$. Sodium molybdate also is preferred. Excellent results were obtained using ammonium dimolybdate, annomium heptamolybdate, sodium molybdate, and the commercial so-called "molybdic acid," which consists primarily of ammonium molybdates.

The reaction preferably is conducted in the presence of an acid in order to maximize the amine molybdate yield. Suitable acids include organic acids containing one to 12 carbon atoms such as formic acid. acetic acid, propionic acid, benzoic acid, and the like; and inorganic acids such as hydrochloric acid, nitric acid, sulfuric and the like. Mixtures of acids may also be used. Excellent results were obtained using formic acid, acetic acid, benzoic acid, hydrochloric acid, nitric acid and sulfuric acid. The amount of acid used may be varied widely from 0 to 10 equivalents and more of acid per equivalent of ammonium or other cation in a particular molybdenum salt. About a 1/1 equivalent ratio is preferred.

Suitable reaction media include water, alcohols such as ethanol or the like, and water/alcohol mixtures. Reaction components may be mixed in any order. A preferred reaction method comprises adding an aqueous solution of an ammonium molybdate or other molybdenum salt to an amine solution in dilute hydrochloric acid, followed by refluxing the reaction mixture for 0.25 to 16 hours, more preferably for 0.25 to 4 hours. Another preferred reaction method comprises charging all reaction components essentially simultaneously to a reaction vessel, followed by refluxing as just described.

The reaction mixture is stirred continuously as a slurry. When the desired reaction time has passed, the mixture is cooled to about room temperature (25° C.). The amine molybdate may be separated by filtration, centrifugation or the like and optionally washed with water, ethanol or a mixture thereof. The amine molybdate may be air dried at about 100°–200° C., or it may be vacuum dried at temperatures up to 150° C. and higher. The amine molybdate is identifiable by means of infrared and x-ray diffraction spectroscopy.

Amines suitable for preparing the amine molybdates used in this invention include polymeric amines, as well as simple amines. The simple amines may contain from 1 to 40 carbon atoms and from 1 to 10 primary, secondary, or tertiary amine groups or a mixture thereof, more preferably from 1 to 6 of such groups. Simple amines include aliphatic, alicyclic, aromatic and heterocyclic amines. Examples of suitable polymeric amines include polyethyleneimine, polyvinylpyridine, polyvinylpyrrolidine, and poly(2,2,4-trimethyl-1-2-dihydroquinolyl).

Examples of suitable simple amines include aliphatic amines such as ethylamine, ethylenediamine, 1,2-propanediamine, 1,3-propanediamine, 1,4-butanediamine, 2-methyl-1,2-propanediamine, 1,5-pentanediamine, 1,6-hexanediamine, 1,7-heptanediamine, 1,8-octanediamine, 1,10-decanediamine, 1,12-dodecanediamine and the like. Also suitable are aliphatic amines such as diethylenetriamine, triethylenetetramine, tetraethylenepentamine, bis(hexamethylene) triamine, 3,3'-iminobispropylamine, guanidine carbonate, and the like. Other suitable amines include alicyclic diamines and polyamines such as 1,2-diaminocyclohexane, 1,8-p-menthanediamine and the like; and aromatic amines such as aniline, N,N-dimethylaniline and the like. Heterocyclic amines may also be used including melamine and substituted melamines; pyridine; piperazine; hexamethylenetetramine; 2,2,4-trimethyl decahydroquinoline; and N-(aminoalkyl)-piperazines wherein each alkyl group contains from 1 to 12 carbon atoms, more preferably 1 to 6 carbon atoms, such as N-(2-aminoethyl)-piperazine and the like.

Melamine and substituted melamines have the formula

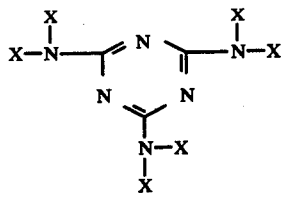

wherein X is hydrogen or an alkyl, alicyclic, aralkyl alkaryl, aryl or heterocyclic group containing from 1 to 10 atoms of C, O, S and/or N. Two X's on each of one or more nitrogen atoms may also be joined together to form a heterocyclic ring such as a morpholino group, for example as in 2,4,6-tri(morpholino)-1,3,5-triazine. Other examples of suitable substituted melamines include N,N',N''-hexaethylmelamine; 2-anilino-4-(2',4'-dimethylanilino)-6-piperidino-1,3,5-triazine; and 2,4,6-tri(N-methylanilino)-1,3,5-triazine.

Excellent results were obtained using ethylamine; ethylenediamine; guanidine carbonate; aniline; N,N-dimethylaniline; melamine; pyridine; piperazine; hexamethylenetetramine; N,N',N''-hexaethylmelamine; 2-anilino-4-(2',4'-dimethylanilino)-6-piperidino-1,3,5-triazine; 2,4,6-tri(N-methylanilino)-1,3,5-triazine; and 2,4,6-tri(morpholino)-1,3,5-triazine. Melamine is preferred since melamine molybdate is both white and highly effective as a smoke retardant. Melamine molybdate also processes easily without discoloring the polymers.

Polymers and Smoke Retarded Compositions

Polymers used in this invention include homopolymers, copolymers and blends thereof; suitable polymers are selected from the group consisting of polyamides, polychloroprene (neoprene), polymonoolefins, halogenated and chlorosulfonated polymonoolefins, polyphenylene oxides, polysulfones, polyvinyl acetate, epihalohydrin polymers, and polymers of acrylonitrile alone or with butadiene and/or styrene.

Suitable polyamides include nylons such as nylon 66 and nylon 6. Examples of polymonoolefins include polyethylene, polypropylene, polyisobutylene, and the like. Preferred monoolefins contain 1 to 8 cabon atoms. The polyphenylene oxide used was poly(2,6-dimethyl-p-phenylene oxide). Halogenated and chlorosulfonated polymonoolefins include chlorinated polyethylene, chlorosulfonated polyethylene and the like. Polysulfones can be produced by the condensation polymerization of bisphenol A and dichlorophenyl sulfone. Preferred epihalohydrin polymers include those described in U.S. Pat. Nos. 3,158,580 and 3,158,581, including polyepichlorohydrin, poly(epichlorohydrin/ethylene oxide), and poly(epichlorohydrin/propylene oxide). Polymers of acrylonitrile alone or with butadiene and/or styrene are polyacrylonitrile, poly(styrene/acrylonitrile) (SAN), poly(acrylonitrile/butadiene) and poly(acrylonitrile/butadiene/styrene) (ABS).

The polymers just described may be prepared by any methods known to the art such as by emulsion, suspension, bulk or solution polymerization. The amine molybdates may be mixed with the polymer emulsion, suspension solution or bulk mass before monomer recovery and/or drying. More preferably, the amine molybdates may be mixed with dry granular or powdered polymers. The polymers and amine molybdates may be mixed thoroughly in granular or powder form in apparatus such as a Henschel mixer, or the like. Alternatively, this step may be eliminated and the mixing done while the polymer mass is fluxed, fused and masticated to homogeneity under fairly intensive shear in or on a mixer apparatus having its metal surface in contact with the material. The fusion temperature and time will vary according to the polymer composition and level of additive compounds but will generally be in the range of about 300° to 400° F. and 2 to 10 minutes.

Smoke retardance may be measured using an NBS Smoke Chamber according to procedures described by Gross et al, "Method for Measuring Smoke from Burning Materials," *Symposium on Fire Test Methods — Restraint & Smoke* 1966, ASTM STP 442, pp. 166–204. Maximum smoke density ($D_m$) is a dimensionless number and has the advantage of representing a smoke density independent of chamber volume, specimen size or photometer path length, provided a consistent dimensional system is used. Percent smoke reduction is calculated using this equation:

$$\frac{D_m/g \text{ of sample} - D_m/g \text{ of control}}{D_m/g \text{ of control}} \times 100.$$

The term "$D_m/g$" means maximum smoke density per gram of sample. $D_m$ and other aspects of the physical optics of light transmission through smoke are discussed fully in the above ASTM publication.

Smoke retardance may be measured quickly using the Goodrich Smoke-Char Test. Test samples may be prepared by dry blending polymer resin and smoke retardant additives. The blend is ground in a liquid $N_2$-cooled grinder to assure uniform dispersion of the smoke retardant additives in the resin. Small (about 0.3g) samples of the polymer blend are pressed into pellets about ¼ inch diameter for testing. Alternatively, test samples may be prepared by blending resin, smoke retardant additives and lubricant(s) or processing aid(s) in a blender such as an Osterizer blender. The blend is milled, pressed into sheets, and cut into small (about 0.3 gram) samples for testing. The test samples are placed on a screen and burned for 60 seconds with a propane gas flame rising vertically from beneath the samples. Sample geometry at a constant weight has been found not to be significant for the small samples used in this test. A Bernz-O-Matic pencil flame burner head is used with gas pressure maintained at about 40 psig. Each sample is immersed totally and continuously in the flame. Smoke from the burning sample rises in a vertical chimney and passes through the light beam of a Model 407 Precision Wideband Photometer (Grace Electronics, Inc., Cleveland, Ohio) coupled with a photometer integrator. Smoke generation is measured as integrated area per gram of sample.

The compositions of this invention may contain the usual compounding ingredients known to the art such as filters, stabilizers, opacifiers, lubricants, processing aids and the like. A substantially larger reduction in smoke then predicted can be obtained frequently when a halogen source is used together with an amine molybdate in the compositions of this invention, particularly in compositions where the principal polymer (e.g., polyvinyl acetate) does not itself contain halogen. Suitable halogen sources include chlorinated paraffin waxes, preferably containing from about 40 to about 75 percent by weight of chlorine, such as those sold under the "Chlorowax" name by Diamond Alkali Co. Also suitable are chlorinated biphenyls and terphenyls; polybrominated hydrocarbons such as hexabromocyclododecane, hexabromocyclododecatriene, tetrabromobutane, dibromoethylbenzene; and other chlorinated and brominated compounds such as hexachloroethane, tris(dibromopropyl) phosphate, pentabromophenol and the like. The amount of halogen source typically is from 0 to 100 weight parts per 100 weight parts of the principal polymer(s) described heretofore.

The following examples illustrate the present invention more fully.

EXAMPLE I

Syntheseis of Melamine Molybdate in Aqueous Medium

Melamine molybdate having a 1/1 molybdenum/-melamine molar ratio was prepared in a non-acid reaction medium as follows. 100 grams of melamine was dissolved in 2.5 liters of distilled water by heating to reflux in a 3-liter round-bottomed flask equipped with a watercooled condenser. 275.30 grams of ammonium heptamolybdate was dissolved in 1-liter of hot distilled water and then added to the first solution. A white precipitate formed immediately.

The reaction mixture was refluxed for 4 hours and thereafter filtered hot through Whatman No. 42 filter paper that was backed by a Macherey, Negel and Company (Duren, Germany) MN-85 filter paper supported on a Buchner funnel. A white solid was separated and washed with three 50 ml water portions and three 50 ml ethanol portions. The solid was dried for about 15 hours at 57° C. and found to weigh 235.01 grams.

A white crystalline solid precipitated from the filtrate after it stood overnight at room temperature. The precipitate was recovered and washed as just described. It was vacuum dried for 1 hour at 70° C. and found to weigh 10.70 grams. Infrared and x-ray diffraction spectroscopic analyses demonstrated that both solids were identical, i.e., both were melamine molybdate. Total product yield was 245.71 grams.

EXAMPLES 2-18

Examples 2-18 summarized in Table I illustrate the production of melamine molybdate having a 1/1 molybdenum/melamine molar ratio using the general reaction and recovery procedures of Example 1 in an aqueous medium.

TABLE I

| Example | Starting Molybdenum Compound(grams)+ | Melamine (grams) | Molybdenum/Melamine Molar Ratio In Reactants | $H_2O$ (ml) | Reaction Time | Melamine Molybdate Yield (grams) |
|---|---|---|---|---|---|---|
| 2 | 2.57 (m) | 2.00 | 0.96 | 100 | 3 min. | 1.50 |
| 3 | 5.14 (m) | 4.00 | 0.96 | 250 | 1 hr | 5.25 |
| 4 | 13.34 (m) | 10.00 | 1.0 | 344 | 4 hr | 7.60 |
| 5 | 10.27 (m) | 4.00 | 1.9 | 275 | 5 min. | 8.15 |
| 6 | 10.27 (m) | 4.00 | 1.9 | 275 | 5 min. | 7.72 |
| 7 | 275.30 | 100.00 | 2.0 | 3500 | 15 min. | 247.22 |
| 8 | 275.30 | 100.00 | 2.0 | 3500 | 35 min. | 245.23 |
| 9 | 10.27 (m) | 4.00 | 1.9 | 275 | 1 hr. | 8.20 |
| 10 | 275.30 | 100.00 | 2.0 | 3500 | 3 hr. | 235.01 |
| 11 | 13.88 | 5.00 | 2.0 | 344 | 4 hr. | 10.76 |
| 12 | 275.30 | 100.00 | 2.0 | 3500 | 4 hr. | 237.67 |
| 13 | 13.34 (m) | 5.00 | 2.00 | 344 | 17 hr. | 9.80 |
| 14 | 7.70 (m) | 2.00 | 2.9 | 150 | 1 min. | 4.50 |
| 15 | 15.41 (m) | 4.00 | 2.9 | 300 | 5 min. | 9.80 |
| 16 | 15.41 (m) | 4.00 | 2.9 | 300 | 1 hr. | 9.83 |
| 17 | 15.41 (m) | 4.00 | 2.9 | 300 | 4 hr. | 10.15 |
| 18 | 13.34 (m) | 3.33 | 3.0 | 344 | 4 hr. | 6.50 |

+Ammonium heptamolybdate used, except where indicated otherwise.
(m) = "Baker 0206 Molybdic Acid" which comprises primarily at least one ammonium molybdate.

EXAMPLES 19-39

Examples 19-39 summarized in Table II illustrate the production of melamine molybdate using the general reaction and recovery procedures of Example 1 in an aqueous HCl medium. The melamine molybdate produced in Examples 19-24 had a 1/1 molybdenum/melamine molar ratio. In examples 26-39 the melamine molybdate produced had a 2/1 molybdenum/melamine molar ratio. The product in Example 25 was a mixture of the 1/1 and 2/1 molybdenum/melamine molar ratio melamine molybdates.

TABLE II

| Example | Starting Ammonium Molybdate (grams)+ | Melamine (grams) | Molybdenum/Melamine Molar Ratio In Reactants | $H_2O$ (ml) | 37% HCl (grams) | Reaction Time | Melamine Molybdate Yield (grams) |
|---|---|---|---|---|---|---|---|
| 19 | 2.80 | 2.00 | 1.0 | 60 | 1.34 | 5 min. | 4.28 |
| 20 | 14.00 | 10.00 | 1.0 | 275 | 6.70 | 15 min. | 21.45 |
| 21 | 14.48 (D) | 10.00 | 1.0 | 275 | 7.81 | 30 min. | 21.88 |
| 22 | 13.48 (D) | 10.00 | 1.0 | 175 | 7.81 | 30 min. | 20.99 |
| 23 | 140.00 | 100.00 | 1.0 | 2750 | 67.0 | 3.3 hr. | 211.23 |
| 24 | 14.00 | 10.00 | 1.0 | 275 | 6.70 | 4 hr. | 21.80 |
| 25 | 21.00 | 10.00 | 1.5 | 288 | 10.05 | 2 hr. | 28.35 |
| 26 | 28.00 | 10.00 | 2.0 | 300 | 13.40 | 15 min. | 32.58 |
| 27 | 28.00 | 10.00 | 2.0 | 200 | 13.40 | 30 min. | 34.45 |
| 28 | 26.95 (D) | 10.00 | 2.0 | 200 | 15.62 | 30 min. | 32.79 |
| 29 | 28.00 | 10.00 | 2.0 | 200 | 13.40 | 30 min. | 33.48 |
| 30 | 28.00 | 10.00 | 2.0 | 150 | 13.40 | 30 min. | 33.48 |
| 31 | 28.00 | 10.00 | 2.0 | 300 | 13.40 | 30 min. | 33.50 |
| 32 | 280.00 | 100.00 | 2.0 | 3000 | 134.0 | 30 min. | 339.55 |
| 33 | 28.00 | 10.00 | 2.0 | 200 | 13.40 | 2 hr. | 33.02 |
| 34 | 26.95 (D) | 10.00 | 2.0 | 300 | 15.63 | 3 hr. | 32.96 |
| 35 | 28.00 | 10.00 | 2.0 | 300 | 13.40 | 4 hr. | 32.58 |
| 36 | 280.00 | 100.00 | 2.0 | 3000 | 134.0 | 4.2 hr. | 333.94 |
| 37 | 28.00 | 10.00 | 2.0 | 150 | 13.40 | 4 hr. | 32.80 |

TABLE II-continued

| Example | Starting Ammonium Molybdate (grams)+ | Melamine (grams) | Molybdenum/Melamine Molar Ratio In Reactants | $H_2O$ (ml) | 37% HCl (grams) | Reaction Time | Melamine Molybdate Yield (grams) |
|---|---|---|---|---|---|---|---|
| 38 | 28.00 | 10.00 | 2.0 | 200 | 13.40 | 16 hr. | 32.70 |
| 39 | 28.00 | 10.00 | 2.0 | 300 | 13.40 | 16 hr. | 32.68 |

+Ammonium heptamolybdate used, except where indicated otherwise (D=ammonium dimolybdate).

EXAMPLE 40

Synthesis of Melamine Molybdate in Aqueous Formic Acid Medium

Melamine molybdate was prepared in the presence of formic acid as follows. 10 grams of melamine, 7.30 grams of formic acid, and 250 ml water were dissolved together by refluxing in a 500 ml. round-bottomed flask equipped with a stirrer and water-cooled condenser. 26.95 grams of ammonium dimolybdate was dissolved in 50 ml hot water and then added to the first solution. A white precipitate formed immediately.

The reaction mixture was refluxed for one hour and filtered hot as in Example 1. A white solid was recovered and washed three times with water. The solid weighed 29.25 grams after being vacuum dried for 3.25 hours at 120° C.

EXAMPLE 41

Synthesis of Melamine Molybdate in Aqueous Acetic Acid Medium

Melamine molybdate was prepared in the presence of acetic acid as follows. 10 grams of melamine, 9.52 grams of acetic acid, and 250 ml water were dissolved together by refluxing in a 500 ml round-bottomed flask equipped with a stirrer and water-cooled condenser. 26.95 grams of ammonium dimolybdate was dissolved in 50 ml. hot water and then added to the first solution. A white precipitate formed immediately.

The reaction mixture was refluxed for one hour, cooled to room temperature (about 25° C.), and filtered through Whatman No. 42 filter paper that was backed by a Macherey, Negal and Company (Duren, Germany) MN-85 filter paper supported on a Buchner funnel. A white solid was recovered and washed three times with water. The solid weighed 28.38 grams after being vacuum dried for 3 hours at 120° C.

EXAMPLE 42

Synthesis of Melamine Molybdate in Aqueous Benzoic Acid Medium

Melamine molybdate was prepared in the presence of benzoic acid as follows. 5 grams of melamine, 9.68 grams of benzoic acid, and 250 ml water were dissolved together by refluxing in a 500 ml round-bottomed flask equipped with a stirrer and water-cooled condenser. 13.47 grams of ammonium dimolybdate was dissolved in 25 ml hot water and then added to the first solution. A white precipitate formed immediately.

The reaction mixture was refluxed for one hour and filtered hot as in Example 1. A white solid was recovered and washed three times with water. The solid weighed 13.04 grams after being vacuum dried for 3 hours at 120° C.

EXAMPLE 43

Synthesis of Ethylamine Molybdate in Aqueous HCl Medium

Ethylamine molybdate having a 1/1 molybdenum/ethylamine molar ratio was prepared in the presence of HCl as follows. 14.29 grams of a 70 wt.% ethylamine aqueous solution, 21.85 grams of a 37 wt.% aqueous HCl solution, and 150 ml water were dissolved together and heated to reflux in a 500 ml. round-bottomed flask equipped with a stirrer and water-cooled condenser. 37.70 grams of ammonium dimolybdate was dissolved in 80 ml hot water and then added to the first solution.

The reaction mixture was refluxed for 1.5 hours, cooled to room temperature (about 25° C.), and filtered as in Example 41. A white solid was recovered and washed four times with water. The solid was vacuum dried for 2 hours at 120° C. The final product was a fluffy white solid weighing 26.68 grams.

EXAMPLE 44

Synthesis of Ethylenediamine Molybdate in Aqueous HCl Medium

Ethylenediamine molybdate having a 2/1 molybdenum/ethylenediamine molar ratio was prepared in the presence of HCl as follows. 5.10 grams ethylenediamine, 16.39 grams of a 37 wt.% aqueous HCl solution, and 125 ml water were dissolved together and heated to reflux in a 500 ml. round-bottomed flask equipped with a stirrer and water-cooled condenser. 28.28 grams of ammonium dimolybdate was dissolved in 53 ml hot water and then added to the first solution.

The reaction mixture was refluxed for 1 hour, cooled to room temperature and filtered as in Example 41. A white solid was recovered and washed three times with water. The solid was vacuum dried for 2 hours at 120° C. The final product was a white solid weighing 21.39 grams. It appeared to be photochromic, changing to a pale pink color after brief exposure to light.

EXAMPLE 45

Synthesis of Guanidine Molybdate In Aqueous HCl Medium

Guanidine molybdate having a 2/1 molybdenum/guanidine molar ratio was prepared in the presence of HCl as follows. 10 grams guanidine carbonate, 21.88 grams of a 37 wt.% aqueous HCl solution, and 250 ml water were dissolved together and heated to reflux in a 500 ml round-bottomed flask equipped with a water-cooled condenser. 37.74 grams of ammonium dimolybdate was dissolved in 70 ml hot water and then added to the first solution.

The reaction mixture was refluxed for 1 hour, cooled to room temperature, and filtered as in Example 41. A yellow solid was recovered and washed three times with water. The solid was vacuum dried for 2 hours at 120° C. The final product was a pale yellow powder weighing 37.50 grams.

EXAMPLE 46

Synthesis of Aniline Molybdate in Aqueous HCl Medium

Aniline molybdate having a 2/1 molybdenum/aniline molar ratio was prepared in the presence of HCl as follows. 10 grams of aniline, 21.16 grams of a 37 wt.% aqueous HCl solution, and 250 ml water were dissolved together and heated to reflux in a 500 ml round-bottomed flask equipped with a stirrer and water-cooled condenser. 36.50 grams of ammonium dimolybdate was dissolved in 68 ml hot water and then added to the first solution.

The reaction mixture was refluxed for 1 hour, cooled to room temperature, and filtered as in Example 41. A light gray solid was recovered and washed three times with water. The solid was vacuum dried for 2.5 hours at 120° C. The final product was a slightly off-white solid weighing 38.01 grams.

EXAMPLE 47

Synthesis of N,N-dimethylaniline Molybdate in Aqueous HCl Medium

N,N-dimethylaniline molybdate having a 2/1 molybdenum/N,N-dimethylaniline molar ratio was prepared in the presence of HCl as follows. 10 grams of N,N-dimethylaniline, 16.26 grams of a 37 wt.% aqueous HCl solution, and 250 ml water were dissolved together and heated to reflux in a 500 ml round-bottom flask equipped with a water-cooled condenser. 28.05 grams of ammonium dimolybdate was dissolved in 52 ml hot water and then added to the first solution.

The reaction mixture was refluxed for 1 hour, cooled to room temperature, and filtered as in Example 41. A solid was recovered and washed three times with water. The solid was vacuum dried for 2.5 hours at 120° C. The final product was a pale bluish-white solid weighing 29.74 grams.

EXAMPLE 48

Synthesis of Pyridine Molybdate in Aqueous HCl Solution

Pyridine molybdate having a 2/1 molybdenum/pyridine molar ratio was prepared in the presence of HCl as follows. 10 grams of pyridine, 24.92 grams of a 37 wt.% aqueous HCl solution, and 150 ml water were dissolved together and heated to reflux in a 500 ml round-bottomed flask equipped with a stirrer and water-cooled condenser. 42.98 grams of ammonium dimolybdate was dissolved in 90 ml hot water and then added to the first solution. A very thick white precipitate formed rapidly.

The reaction mixture was refluxed for 1 hour, cooled to room temperature, and filtered as in Example 41. A white solid was recovered and washed four times with water. The solid was vacuum dried for about 2.25 hours at 120° C. The final product was a hydrated white solid weighing 57.84 grams.

EXAMPLE 49

Synthesis of Piperazine Molybdate in Aqueous Solution

Piperazine molybdate having a 2/1 molybdenum/piperazine molar ratio was prepared as follows. 22.55 grams of piperazine hydrate was dissolved in 50 ml water heated near reflux temperature. 39.09 grams of commercial, so-called "molybdic acid" (actually at least one ammonium molybdate) was dissolved in 275 ml water heated to reflux temperature. The first solution was added to the second solution. A voluminous white precipitate formed rapidly.

The reaction mixture was refluxed for 1.5 hours and filtered hot as in Example 1. A white solid was recovered and washed three times with water and three times with ethanol. The solid was vacuum dried for about 16 hours at 73° C. The final product was 11.77 grams of a low density white powder. It appeared to be photochromic, turning pink after brief exposure to light.

EXAMPLE 50

Synthesis of Piperazine Molybdate in Aqueous HCl Solution

Piperazine molybdate having a 2/1 molybdenum/piperazine molar ratio was prepared in the presence of HCl as follows. 22.55 grams of piperazine hydrate, 22.86 grams of a 37 wt.% aqueous HCl solution, and 100 ml water were dissolved together and heated to reflux in a 500 ml round-bottomed flask equipped with a stirrer and water-cooled condenser. 39.46 grams ammonium dimolybdate was dissolved in 85 ml hot water and then added to the first solution. A thick precipitate formed rapidly.

The reaction mixture was refluxed for 20 minutes, cooled to room temperature, and filtered as in Example 41. A white solid was vacuum dried for 6 hours at 120° C. The final product was a white solid weighing 36.10 grams. It appeared to be photochromic, turning pink after brief exposure to light.

EXAMPLE 51

Synthesis of Hexamethylenetetramine Molybdate in Aqueous Solution

Hexamethylenetetramine molybdate having a 2/1 molybdenum/hexamethylenetetramine molar ratio was prepared as follows. 10 grams of hexamethylenetetramine was dissolved in 100 ml water heated near reflux temperature. 24.01 grams of commercial, so-called "molybdic acid" (actually at least one ammonium molybdate) was dissolved in 169 ml water heated to reflux temperature. The first solution was added to the second solution.

The reaction mixture was refluxed for about 19 hours, cooled to room temperature, and filtered as in Example 41. A white solid was recovered and washed with water and ethanol. The solid was vacuum dried for about 3 hours at 73° C. The final product was a slightly off-white powder weighing 14.23 grams.

EXAMPLE 52

Synthesis of Hexamethylenetetramine Molybdate in Aqueous HCl Solution

Hexamethylenetetramine molybdate having a 2/1 molybdenum/hexamethylenetetramine molar ratio was prepared in the presence of HCl as follows. 10 grams of hexamethylenetetramine, 14.05 grams of a 37 wt.% aqueous HCl solution, and 100 ml water were dissolved together and heated to reflux in a 500 ml round-bottomed flask equipped with a stirrer and water-cooled condenser. 24.24 grams ammonium dimolybdate was dissolved in 50 ml hot water. The second solution was added to the first solution, and a thin white precipitate formed rapidly.

The reaction mixture was refluxed for 1 hour, cooled to room temperature, and filtered as in Example 41. A white solid was recovered and washed four times with water. The solid weighed 27.50 grams after being vacuum dried for 2 hours at 120° C.

EXAMPLE 52

Synthesis of N,N',N''-Hexaethylmelamine Molybdate in Aqueous HCl Medium

N,N',N''-hexaethylmelamine molybdate having a 2/1 molybdenum/N,N',N''-hexaethylmelamine molar ratio was prepared in the presence of HCl as follows. 10 grams N,N',N''-hexaethylmelamine, 6.69 grams of a 37 wt.% aqueous HCl solution, and 250 ml water were mixed together and heated to reflux in a 500 ml round-bottomed flask equipped with a stirrer and water-cooled condenser. 11.54 grams of ammonium dimolybdate was dissolved in 25 ml hot water and then added to the refluxing mixture. A bright yellow precipitate formed immediately.

The reaction mixture was refluxed for 20 minutes, cooled to room temperature, and filtered as in Example 41. A bright yellow solid was recovered and washed three times with water. The solid weighed 19.32 grams after being vacuum dried for 2.25 hours at 120° C.

EXAMPLE 54

Synthesis of 2-Anilino-4-(2',4'-dimethylanilino)-6-piperidino-1,3,5-triazine Molybdate in Aqueous HCl Medium 2-Anilino-4-(2',4',-dimethylanilino)-6-piperidino-1,3,5-triazine is a substituted melamine having the formula

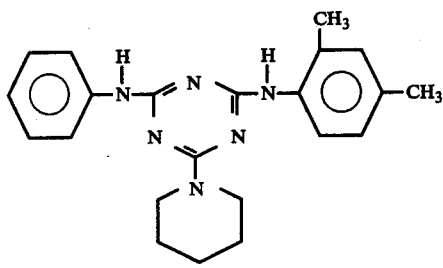

2-Anilino-4-(2',4'-dimethylanilino)-6-piperidino-1,3,5-triazine molybdate having a 2/1 molar ratio of molybdenum to substituted melamine was prepared in the presence of HCl as follows. 5 grams of the substituted melamine, 2.63 grams of a 37 wt.% aqueous HCL solution, 125 ml water and 160 ml ethanol were dissolved together by refluxing in a 500 ml round-bottomed flask equipped with a stirrer and water-cooled condenser. 4.54 grams of ammonium dimolybdate was dissolved in 10 ml hot water and then added to the first solution. An off-white precipitate formed immediately.

The reaction mixture was refluxed for 20 minutes, cooled to room temperature and filtered as in Example 41. An off-white solid was recovered and washed twice with a 50/50 by volume ethanol/water solution and twice with water. The solid weighed 8.22 grams after being vacuum dried for 2.5 hours at 120° C.

EXAMPLE 55

Synthesis of 2,4,6-Tri(N-methylanilino)-1,3,5-triazine Molybdate in Aqueous HCl Medium 2,4,6-Tri(N-methylanilino)-1,3,5-triazine is a substituted melamine having the formula

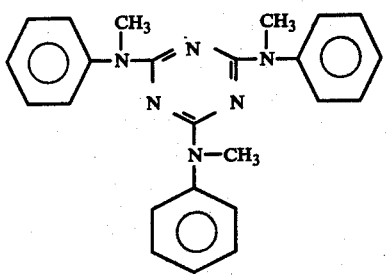

2,4,6-Tri(N-methylanilino)-1,3,5-triazine molybdate having a 2/1 molar ratio of molybdenum to substituted melamine was prepared in the presence of HCl as follows. 7 grams of substituted melamine, 3.48 grams of a 37 wt.% aqueous HCl solution, 75 ml water and 100 ml ethanol were dissolved together by refluxing in a 500 ml round-bottomed flask equipped with a stirrer and water-cooled condenser. 6 grams of ammonium dimolybdate was dissolved in 12 ml hot water and then added to the first solution. A yellow precipitate formed immediately.

The reaction mixture was refluxed for 1.25 hours, cooled to room temperature and filtered as in Example 41. A yellow solid was recovered and washed twice with a 50/50 by volume ethanol/water solution and twice with water. The solid weighed 11.90 grams after being vacuum dried for 4.25 hours at 120° C.

EXAMPLE 56

Synthesis of 2,4,6-tri(morpholino)-1,3,5-triazine Molybdate in Aqueous HCl Medium 2,4,6-Tri(morpholino)-1,3,5-triazine is a substituted melamine having the formula

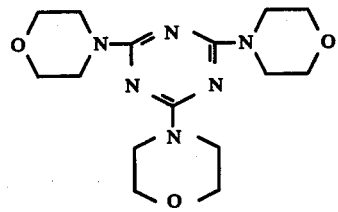

2,4,6-Tri(morpholino)-1,3,5-triazine molybdate having a 2/1 molar ratio of molybdenum to substituted melamine was prepared in the presence of HCl as follows. 3.50 grams of substituted melamine, 2.05 grams of a 37 wt.% aqueous HCl solution, 88 ml water and 88 ml ethanol were dissolved together by refluxing in a 500 ml round-bottomed flask equipped with a stirrer and water-cooled condenser. 3.50 grams of ammonium dimolybdate was dissolved in 8 ml hot water and then added to the first solution. A bright yellow precipitate formed immediately.

The reaction mixture was refluxed for 1 hour, cooled to room temperature and filtered as in Example 41. A yellow solid was recovered and washed twice with a 50/50 by volume ethanol/water solution and twice with water. The solid weighed 6.20 grams after being vacuum dried for 2.5 hours at 120° C.

EXAMPLE 57

Synthesis of 2,2,4-Trimethyl decahydroquinoline Molybdate in Aqueous HCl Solution 2,2,4-Trimethyl decahydroquinoline molybdate having a 2/1 molybdenum/2,2,4-trimethyl decahydroquinoline molar ratio was prepared as follows. 10 grams 2,2,4-trimethyl decahydroquinoline, 16.30 grams of a 37 wt.% aqueous HCl solution and 250 ml water were dissolved together and heated to reflux in a 500 ml round-bottomed flask equipped with a stirrer and water-cooled condenser. 28.12 grams ammonium dimolybdate was dissolved in 50 ml hot water. The second solution was added to the first solution. A yellow precipitate formed immediately.

The reaction mixture was refluxed for 15 minutes, cooled to room temperature, and filtered as in Example 41. A yellow solid was recovered and washed three times with water. A fluffy yellow solid weighing 29.97 grams was produced after being vacuum dried for 2.25 hours at 70° C.

EXAMPLES 58–70

Examples 58–70 demonstrate the utility of melamine molybdate as a smoke retardant in selected organic polymers. The Goodrich Smoke Char Test was used, with powdered blend samples being pressed into pellets and testing done as described heretofore. In each example the recipe consisted of 100 weight parts of polymer and (except for the control) variable weight amounts of melamine molybdate and an approximately 70% chlorinated paraffin wax, the latter compound sold as "Chlorowax 70" by Diamond Alkali Company.

Test results are summarized in TABLE III.

TABLE III

| Example | Polymer Name | Manufacturer's Code | Melamine Molybdate (phr) | "Chlorowax 70" (phr) | Smoke Formation Per Gram of Sample | Smoke Reduction (%) |
|---|---|---|---|---|---|---|
| 58 | Nylon | duPont Zytel 101 | — | — | 2.6 | — |
|  | Nylon | duPont Zytel 101 | 5 | 0.8 | 69 | — |
| 59 | Polychloroprene | Goodyear Neoprene W | — | — | 156 | — |
|  | Polychloroprene | Goodyear Neoprene W | 10 | — | 102 | 35 |
| 60 | Polyethylene | Masonite Microthene F | — | — | 28 | — |
|  | Polyethylene | Masonite Microthene F | 5 | — | 21 | 25 |
| 61 | Polypropylene | Union Carbide UC153908 | — | — | 90 | — |
|  | Polypropylene | Union Carbide UC153908 | 5 | — | 73 | 19 |
| 62 | Chlorosulfonated Polyethylene | duPont Hypalon 45 | — | — | 139 | — |
|  | Chlorosulfonated Polyethylene | duPont Hypalon 45 | 10 | — | 97 | 30 |
|  | Chlorosulfonated Polyethylene | duPont Hypalon 45 | 10 | 15 | 46 | 67 |
| 63 | PPO[+] | General Electric | — | — | 93 | — |
|  | PPO[+] | General Electric | 10 | — | 27 | 71 |
|  | PPO[+] | General Electric | 10 | 15 | 34 | 63 |
| 64 | Polysulfone | Union Carbide Bakelite D1700 | — | — | 18 | — |
|  | Polysulfone | Union Carbide Bakelite D1700 | 5 | — | 10 | 44 |
| 65 | Poly(vinyl acetate) | Polysciences, Inc. 2025 | — | — | 92 | — |
|  | Poly(vinyl acetate) | Polysciences, Inc. 2025 | 10 | — | 42 | 54 |
|  | Poly(vinyl acetate) | Polysciences, Inc. 2025 | 10 | 15 | 8 | 91 |
| 66 | Polyepichlorohydrin | B.F.Goodrich Hydrin® 100 | — | — | 67 | — |
|  | Polyepichlorohydrin | B.F.Goodrich Hydrin® 100 | 10 | — | 29 | 57 |
| 67 | Polyacrylonitrile | Polysciences, Inc. 3914 | — | — | 49 | — |
|  | Polyacrylonitrile | Polysciences, Inc. 3914 | 10 | — | 32 | 35 |
|  | Polyacrylonitrile | Polysciences, Inc. 3914 | 10 | 15 | 13 | 73 |
| 68 | Poly(styrene/acrylonitrile) | Dow Chemical Co. Tyril MX-4582.03 | — | — | 79 | — |
|  | Poly(styrene/acrylonitrile) | Dow Chemical Co. Tyril MX-4582.03 | 10 | — | 38 | 52 |
|  | Poly(styrene/acrylonitrile) | Dow Chemical Co. Tyril MX-4582.03 | 10 | 15 | 49 | 38 |
| 69 | Poly(acrylonitrile/butadiene) | B.F.Goodrich Hycar® 1422 | — | — | 88 | — |
|  | Poly(acrylonitrile/butadiene) | B.F.Goodrich Hycar® 1422 | 10 | — | 77 | 13 |
|  | Poly(acrylonitrile/butadiene) | B.F.Goodrich Hycar® 1422 |  |  |  |  |
| 70 | ABS[++] | Borg-Warner Blendex 311 | — | — | 141 | — |
|  | ABS[++] | Borg-Warner Blendex 311 | 10 | — | 11 | 92 |
|  | ABS[++] | Borg-Warner Blendex 311 | 10 | 15 | 15 | 89 |

[+] Poly(2,6-dimethyl-p-phenylene oxide)
[++] Acrylonitrile/butadiene/styrene terpolymer The improved smoke retardant polymer compositions of this invention are useful wherever smoke resistance is desirable, such as in carpets, house siding, plastic components for airplane interiors, and the like. Of course, overall suitability for a particular use will depend upon other factors as well, such as comonomer type and level, compounding ingredient type and level, polymer particle size, and the like.

I claim:
1. A smoke retarded composition comprising
   (A) a smoke retardant amount of at least one amine molybdate, the amine used in preparing said amine molybdate containing from 1 to 40 carbon atoms and from 1 to 10 primary, secondary or tertiary amine groups or a mixture thereof, and
   (B) at least one polymer selected from the group consisting of, polychloroprene, polymonoolefins, halogenated and chlorosulfonated polymonoolefins, poly(vinylacetate), and polymers of acrylonitrile alone or with butadiene and/or styrene.
2. A composition of claim 1 wherein said amine molybdate is present in an amount from about 0.01 to about 20 weight parts per 100 weight parts of polymer.
3. A composition of claim 2 wherein said amine molybdate is a heterocyclic amine molybdate.
4. A composition of claim 3 wherein the heterocyclic amine used in producing said heterocyclic amine molybdate is melamine or a substituted melamine having the formula

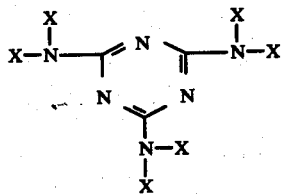

X being hydrogen or an alkyl, alicyclic, aralkyl, alkaryl, aryl or heterocyclic group containing from 1 to 10 atoms of carbon, oxygen, sulfur and/or nitrogen, and with two X's on each of one or more nitrogen atoms optionally being joined together to form a heterocyclic ring.
5. A composition of claim 4 wherein the heterocyclic amine molybdate is melamine molybdate.
6. A composition of claim 5 wherein said polymer is polychloroprene.
7. A composition of claim 5 wherein said polymer is a polymonoolefin.
8. A composition of claim 7 wherein said polymonoolefin is polyethylene.
9. A composition of claim 7 wherein said polymonoolefin is polypropylene.
10. A composition of claim 5 wherein said polymer is a halogenated or chlorosulfonated polymonoolefin.
11. A composition of claim 10 wherein said chlorosulfonated polymonoolefin is chlorosulfonated polyethylene.
12. A composition of claim 5 wherein said polymer is poly(vinyl acetate).
13. A composition of claim 5 wherein said polymer is a polymer of acrylonitrile alone or with butadiene and/or styrene.
14. A composition of claim 13 wherein said polymer of acrylonitrile is polyacrylonitrile.
15. A composition of claim 13 wherein said polymer of acrylonitrile is poly(styrene/acrylonitrile).
16. A composition of claim 13 wherein said polymer of acrylonitrile is poly(acrylonitrile/butadiene).
17. A composition of claim 13 wherein said polymer of acrylonitrile is an acrylonitrile/butadiene/styrene terpolymer.
18. A composition of claim 1 wherein a halogen source is additionally present.
19. A composition of claim 18 wherein said halogen source is a chlorinated paraffin wax.